United States Patent [19]

Winkel et al.

[11] Patent Number: 5,095,045
[45] Date of Patent: Mar. 10, 1992

[54] PLASTICS WHICH CURE IN A SERIES OF STEPS HAVING URETHANE, UREA, SILOXANE AND ACRYLATE GROUPS

[75] Inventors: Jens Winkel, Cologne; Peter Schwabe, Leverkusen; Hanns-Peter Muller, Bergisch Gladbach, all of Fed. Rep. of Germany

[73] Assignee: Bayer Aktiengesellschaft, Leverkusen, Fed. Rep. of Germany

[21] Appl. No.: 549,783

[22] Filed: Jul. 9, 1990

[30] Foreign Application Priority Data

Jul. 22, 1989 [DE] Fed. Rep. of Germany ....... 3924308

[51] Int. Cl.$^5$ .............................................. C08L 75/02
[52] U.S. Cl. ...................................... 523/115; 528/26; 525/185; 524/728; 522/77
[58] Field of Search ............... 528/26; 525/185; 524/728; 523/115; 522/77

[56] References Cited

U.S. PATENT DOCUMENTS 3,632,557  1/1972  Brode ................................. 528/59
4,322,517  3/1982  Deubzer ............................. 528/26

Primary Examiner—Maurice J. Welsh
Assistant Examiner—Rachel Johnson
Attorney, Agent, or Firm—Sprung Horn Kramer & Woods

[57] ABSTRACT

A hard, resistant material formed by mixing and curing a) at least one polyfunctional silicopolyether,
b) at least one monomer which can be subjected to free-radical curing,
c) at least one catalyst for polymerization of the free-radical monomers at high temperature, low temperature or under the influence of light, and
d) at least one catalyst for the condensation of the silicopolyether.

6 Claims, No Drawings

PLASTICS WHICH CURE IN A SERIES OF STEPS HAVING URETHANE, UREA, SILOXANE AND ACRYLATE GROUPS

The invention relates to novel plastics which cure in two steps; they are materials which, starting from a liquid state, can be converted in a controlled manner into an elastic body which can subsequently be cured to give a hard, resistant material. Such materials are of interest, inter alia, in the field of dentistry, for example for making artificial teeth or parts of teeth.

Systems which cure in a series of steps are known in principle. For example, DE-PS (German Patent Specification) 3,506,020 describes a method for making artificial teeth or parts of teeth, in which method diisocyanates are reacted with polyols in the presence of methacrylate monomers to give polyurethane gels which can subsequently be cured by free-radical polymerization. Systems of this type have the disadvantage that the formation of the polyurethane gel must take place with the exclusion of moisture in order to avoid undesirable side-reactions, and they are therefore unsuitable for use in a humid environment, as is the case, for example, with use in the mouth.

Plastics are furthermore known for making temporary tooth replacement, as are described, for example, in the dissertation by H. Frey (H. Frey: Physikalische Eigenschaften verschiedener Kunststoffe für provisorischen Zahnersaz in der Kronen- und Brückenprothetik, [Physical properties of various plastics for temporary tooth replacement in crown and bridge prosthetics], Zurich 1980, G. Bohi, Buch- und Offsetdruck, Zurich), and they are frequently used in dental medicine. The systems consist of a polymethacrylate powder which is subjected to incipient swelling in low-molecular methacrylic esters. This gel can subsequently be subjected to free-radical curing. To achieve a sufficiently high swelling rate, it is necessary to use low-molecular methacrylic esters, which are highly odorous and often result in allergic responses.

It has now been found that mixtures of silicopolyethers, as are described in DE-PS (German Published Specification) 3,636,924, and of monomers which can be subjected to free-radical curing, can cured in two steps, using at least two suitable catalysts. In the first step of this process, the silicopolyether reacts in the presence of acids to give a gel which can be polymerized in a second step by means of free-radical starters to give a hard, resistant material. The materials according to the invention are generally characterized by the fact that they contain a) at least one polyfunctional silicopolyether,
b) at least one monomer which can be subjected to free-radical curing,
c) at least one catalyst for polymerization of the free-radical monomers at high temperature, low temperature or under the influence of light, and
d) at least one catalyst for the condensation of the silicopolyether.

The invention preferably relates to plastics which can be cured in a series of steps and which consist of polyaddition products, containing ether, urethane and urea groups and having alkoxysilyl terminal groups of a mostly linear molecular structure, with exclusively aliphatically or cycloaliphatically bonded ether, urethane and urea segments, having a mean molecular weight Mn of 800–20,000, characterized in that they contain a) polyether groups in an amount of 25 to 90 parts by weight, preferably of 50 to 80 parts by weight, per 100 parts by weight of polyaddition product,
b) urethane groups

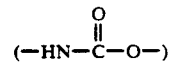

in an amount of 0.5 to 10 parts by weight, preferably of 1 to 8 parts by weight, per 100 parts by weight of polyaddition product,
c) urea groups

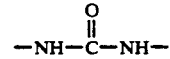

in an amount of 0.5 to 10 parts by weight, preferably 1–8 parts by weight, per 100 parts by weight of polyaddition product, and
d) terminal alkoxysilyl groups

in an amount of 1 to 25 parts by weight, preferably 2 to 10 parts by weight, per 100 parts by weight of polyaddition product, the alkoxysilyl groups in the polyadduct being introduced by means of the following compounds and having the following formula:

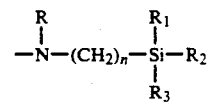

where
n represents the numbers 1 to 6, preferably the number 3,
R denotes hydrogen or —(CH$_2$)$_n$—SiR$_1$R$_2$R$_3$,
R$_1$ denotes C$_1$-C$_4$-alkoxy, preferably methoxy or ethoxy,
R$_2$ and R$_3$ have the same meaning as R$_1$ and additionally represent the methyl or the ethyl group.

The invention preferably relates to plastics which can be cured in a series of steps and which consist of at least one silicopolyether, at least one monomer which can be subjected to free-radical curing, and at least one catalyst for polymerization under the influence of high temperature, low temperature or light, and at least one catalyst for the condensation of the silicopolyether.

The silicopolyethers which can be used according to the invention can be prepared by reacting aliphatic and/or cycloaliphatic diisocyanates with dihydroxypolyethers of a mean molecular weight range Mn of from 300 to 6,000, in which reaction aliphatic and/or cycloaliphatic dihydric alcohols of a mean molecular weight Mn of from 62 to <300 can optionally additionally be added, and by reacting the resulting prepolymers with alkoxysilylmonoamines, in which reaction aliphatic and/or cycloaliphatic diamines containing primary amino groups and having a molecular weight Mn of 60 to 300 can optionally also be used, by a process in which a) alkoxysilylmonoamines of the formula $$HRN-(CH_2)_n-SiR_1R_2R_3$$

where the meanings are as designated above, are added, in which process furthermore b) 0.05 to 1.5, preferably 0.1 to 0.5, part by weight of the diisocyanate, 0 to 0.6 preferably 0 to 0.2, part by weight of the dihydric alcohol, 0.02 to 0.40, preferably 0.05 to 0.2, part by weight of the alkoxysilylmonoamine and 0 to 0.6, preferably 0 to 0.2, part by weight of the diamine, are employed per part by weight of dihydroxypolyether.

The components are reacted at temperatures of from 20° to 150° C., preferably of from 60° to 120° C.

The diamines which are employed if necessary, serve to adjust the specifically desired molecular weight.

Suitable diisocyanates are, in particular, those having aliphatically and/or cycloaliphatically bonded isocyanate groups of the formula $Q(NCO)_2$ in which Q represents an aliphatic hydrocarbon radical having 2 to 12 carbon atoms or a cycloaliphatic or mixed aliphatic-cycloaliphatic hydrocarbon radical having 4 to 15 carbon atoms.

Examples of diisocyanates of this type are ethylene diisocyanate, tetramethylene diisocyanate, hexamethylene diisocyanate, dodecamethylene diisocyanate, cyclobutane 1,3-diisocyanate, cyclohexane 1,3-diisocyanate, cyclohexane 1,4-diisocyanate or 1-isocyanato-3,3,5-trimethyl-5-isocyanatomethyl-cyclohexane, or any desired mixtures of diisocyanates of this type. Cycloaliphatic, or mixed aliphatic-cycloaliphatic diisocyanates, are preferably employed in the process according to the invention. 1-Isocyanato-3,3,5-trimethyl-5-isocyanatomethyl-cyclohexane(isophoronediisocyanate) is particularly preferred.

Suitable dihydroxypolyethers are likewise those of the type known per se, and they are prepared, for example, by polymerizing epoxides, such as ethylene oxide, propylene oxide, butylene oxide, tetrahydrofuran, styrene oxide or epichlorohydrin, with themselves, for example in the presence of $BF_3$, or by an addition reaction of these epoxides, if appropriate as a mixture or in succession, with starting components having reactive hydrogen atoms, such as alcohols or amines, for example water, ethylene glycol, propylene 1,3-glycol or propylene 1,2-glycol, 4,4'-dihydroxydiphenylpropane or aniline. In many cases, those polyethers are preferred which have mainly primary OH groups (up to 90% by weight, based on all OH groups present in the polyether).

Preferred suitable diamines are aliphatic, cycloaliphatic or mixed aliphatic - cycloaliphatic diamines of a molecular weight range of 60 to 300 which have primary amino groups. Examples are ethylenediamine, tetramethylene diamine, hexamethylenediamine, 4,4'-diamino-dicyclohexylmethane, 1,4-diaminocyclohexane, 4,4'-diamino-3,3,-dimethyl-dicyclohexylmethane or 1-amino-3,3,5-trimethyl-5-aminomethyl-cyclohexane (isophoronediamine). 4,4'-Diaminodicyclohexylmethane or isophoronediamine, which has been mentioned last, are very particularly preferably employed.

Suitable dihydric alcohols are, for example, ethylene glycol, propylene 1,2-glycol and propylene 1,3-glycol, butylene 1,4-glycol and butylene 2,3-glycol, hexane 1,6-diol, octane 1,8-diol, neopentyl glycol, cyclohexane dimethanol, 1,4-bis-hydroxymethyl-cyclohexane, 2-methyl-1,3-propanediol, 3-methylpentane-1,5-diol, further diethylene glycol, triethylene glycol, tetraethylene glycol, polyethylene glycols, dipropylene glycol, polypropylene glycols, dibutylene glycols and polybutylene glycols.

Suitable monoamines are likewise known, these preferably being the γ-aminopropyl-tri-$C_1$-$C_4$alkoxysilanes or the bis-(3-$C_1$-$C_4$-alkoxysilylpropyl)-amines, which are easily accessible industrially, and γ-aminopropyl-triethoxysilane is very particularly preferred.

Suitable according to the invention are also mixtures of the described polyaddition product with a wetting agent, wetting agents which are preferably used being tetrasilicic esters, in particular tetraethoxysilane, and polyalkoxypolysiloxanes.

It is possible to employ 0.01 to 5, preferably 0.1 to 1, parts by weight of the wetting agent per part by weight of the polyaddition product.

This mixture is prepared in a manner known to the expert, for example by mixing the components at room temperature, if appropriate at a moderately increased temperature of up to 60° C.

Comonomers which are suitable are basically all monomers which can be subjected to free-radical curing.

Particularly suitable for this purpose are the methacrylates in monofunctional or polyfunctional form, which are known per se and which can be employed on their own or in mixtures. Examples are methyl methacrylate, isobutyl methacrylate, cyclohexyl methacrylate, ethylene glycol dimethacrylate, diethylene glycol dimethacrylate, polyethylene glycol dimethacrylate, butanediol dimethycrylate, hexanediol dimethacrylate, decanediol dimethacrylate, dodecanediol dimethacrylate, bisphenol A dimethacrylate, trimethylolpropane trimethacrylate, but also bis-GMA as well as the reaction products of isocyanates, in particular di- and/or tri-isocyanates, and methacrylates containing OH groups. Examples of the latter are the reaction products of 1 mole of hexamethylene diisocyanate with 2 moles of 2-hydroxyethyl methacrylate, of 1 mole of tris (6-isocyanatohexyl)biuret with 3 moles of hydroxyethyl methacrylate, and of 1 mole of trimethylhexamethylene diisocyanate with 2 moles of hydroxyethyl methacrylate. The proportion of these compounds in the mixture with the silicopolyether is between 10 and 90 percent by weight, preferably between 50 and 80 percent by weight.

The compounds can be cured using catalysts known per se. For example, in the case of high-temperature polymerization, using peroxides, such as dibenzoyl peroxide, dilauryl peroxide, tert.-butyl peroctoate or tert.-butyl perbenzoate, but also using α,α-azo-bis(isobutyroethyl ester)-benzopinacol and 2,2'-dimethylbenzopinacol.

Alternatively, catalysts can be employed which can be activated by means of radiation. The use of a photosensitizer in conjunction with a reducing agent is preferred. Examples of photosensitizers are α-diketones, such as 9,10-phenanthrenequinone, diacetyl, furil, anisil, 4,4'-dichlorobenzil and 4,4'-dialkoxybenzil. Camphorquinone is preferably used. Examples of reducing agents are amines, such as cyanoethylmethylaniline, dimethylaminoethyl methacrylate, n-butylamine, triethylamine, triethanolamine, N,N-dimethylaniline or N-methyldiphenylamine.

A system which is suitable for the so-called redox polymerization is a system of a compound of the peroxide type and of a reducing agent, for example on the basis of tertiary aromatic amines. Examples of peroxides are: dibenzoyl peroxide, dilauroyl peroxide and di-4-chlorobenzoyl peroxide.

Examples of tertiary aromatic amines which may be mentioned are N,N-dimethyl-p-toluidine, bis-(2-hydroxyethyl)-p-toluidine, bis-(2-hydroxyethyl)-3,5-dimethylaniline and N-methyl-N-(2-methylcarbamoyloxypropyl)-3,5-dimethylaniline.

Before use, the peroxide- and amine-containing monomer mixtures are stored separately.

The catalysts mentioned are used in amounts of 0.01 to 10% by weight, based on the material which can be polymerized, in particular in amounts of 0.01 to 5% by weight.

The elastic intermediate state is brought about by polycondensation of polyaddition products containing ethers, urethane or urea groups, with alkoxysilyl terminal groups, as are described in DE-PS (German Patent Specification) 3,636,974. The silicopolyethers can be cured by inorganic and/or organic acids. Suitable examples are acid ion-exchangers, phosphoric acid, dibutylphosphoric acid, dilute sulphuric acid, tartaric acid, citric acid, adipic acid, hydrochloric acid, sulphonic acids, etc. Hydrochloric acid is preferred.

Various acid contents make it possible to adjust the materials to the desired curing time.

Depending on the intended use of the materials, they can also contain inorganic or organic fillers. Examples of suitable inorganic fillers are:

Rock crystal, cristobalite, quartz glass, highly-disperse silica, aluminium oxide and glass ceramics, for example glass ceramics containing lanthan and zirconium (DE-PS (German Patent Specification) 2,347,591). It is preferred to pretreat the inorganic fillers with a binder to improve bonding to the polymer matrix of the polymethacrylate. For example, binding can be achieved by a treatment with organosilicon compounds (Progress in Organic Coatings 11, 297-308 (1983)). It is preferred to employ 3-methacryloyloxypropyltrimethoxysilane. The concomitant use of several fillers which differ in their particle diameter and/or have different silane content can also be advantageous.

In general, the proportion of filler in the mixture is 5 to 80% by weight, preferably 40 to 70% by weight. It is also possible to add organic polymers or copolymers to the material. Furthermore, the customary auxiliaries, such as stabilizers, light screens and colorants can also be present. The following composition of component A may be mentioned by way of example.

100 parts by weight of component A contain:
a) 15-60 parts by weight of silicopolyether
b) 40-70 parts by weight of polymerizable vinyl compounds
c) 0-70 parts by weight of fillers
d) 0-5 parts by weight of free-radical polymerization initiator
e) 0-5 parts by weight of auxiliaries B mentioned.

100 parts by weight of component B contain:
f) 5-30 parts by weight of an organic or inorganic acid
g) 0-10 parts by weight of water
h) 0-10 parts by weight of vinyl compounds
i) 0-70 parts by weight of filler The following examples are intended to further illustrate the invention.

EXAMPLE 1

800 g (0.4 mol of OH) of a linear polyether of MW 4,000 (prepared by polyaddition of 87 parts by weight of propylene oxide onto propylene glycol, followed by polyaddition of 13 parts by weight of ethylene oxide) are dehydrated under a water-pump vacuum for 30 minutes at 120° C. After this, 88.8 g (0.8 mol of NCO) of isophorone diisocyanate (named IPDI below) are added to the batch, and the entire mixture is stirred for 4 hours at 120° C. to 140° C. under nitrogen. The NCO number of the prepolymer is subsequently determined.

NCO found: 1.70%. NCO calculated: 1.89%.

88.4 g (0.4 mol) of 3-aminopropyltriethoxysilane are then added dropwise at 30° C. within 30 minutes under nitrogen to the stirred prepolymer. In this process, the temperature of the mixture rises to 50° C. The mixture is subsequently allowed to afterreact for 30 minutes at 60° C. NCO is no longer detectable by means of IR spectroscopy in the resulting polyurethane-polyurea. In this manner, a virtually colorless, clear, viscous product having a —HN—CO—NH— content of 1.237% by weight and a content of terminal alkoxysilyl groups of 6.22% by weight is obtained after cooling.

EXAMPLE 2

1,000 g (0.5 mol of OH) of a linear polyether of MW 4,000 (prepared by polyaddition of 70 parts by weight of propylene oxide onto propylene glycol and followed by polyaddition of 30 parts by weight of ethylene oxide) are dehydrated as in Example 1. At 40° C., 111 g (1 mol of NCO) of IPDI are added to the batch all at once, followed by 1 drop of zinc octoate. The stirred batch is heated to 110° C. under nitrogen and maintained at this temperature for 40 minutes. The NCO number of the prepolymer is subsequently determined.

NCO found: 1.69%. NCO calculated: 1.89%.

After the batch has been cooled to 60° C., 110.5 g (0.5 mol) of 3-aminopropyl-triethoxysilane are added dropwise under nitrogen within 10 minutes, while stirring. During this process, the temperature of the batch rises to 75° C. The batch is allowed to afterreact for 30 minutes without further heating. Free NCO can no longer be detected, by IR spectroscopy in the resulting polyurethane-polyurea. The polyurethane-polyurea has a —HN—CO—NH-content of 2.37% by weight and a content of terminal alkoxysilyl groups of 6.22%, is colorless and clear and has a good pourability.

EXAMPLE 3

1,000 g (0.5 mol of OH) of a linear polyether of MW 2,000 (prepared by polyaddition of equal parts by weight of propylene oxide and ethylene oxide onto propylene glycol) are dehydrated as in Example 1. 166.5 g (1.5 mol of NCO) of IPDI are added to the batch all at once at 80° C., followed by 1 drop of zinc octoate. The batch is stirred for 4 hours at 120 C under nitrogen. The NCO number of the prepolymer is subsequently determined.

NCO found: 1.79%. NCO calculated: 1.80%.

After the mixture has cooled to 60° C., 110.5 g (0.5 mol) of 3-aminopropyl-triethoxysilane are added dropwise under nitrogen, while stirring. After this, the batch is free from NCO. The polyurethane-polyurea is a colourless, clear and highly viscous liquid having a —HN—CO—NH— content of 2.27% by weight and a content of terminal alkoxysilyl groups of 5.95% by weight.

EXAMPLE 4

The procedure of Example 3 is followed, with the difference that 639 g of tetraethoxysilane are added to the resulting polyurethane-polyurea after it has been prepared. The homogeneous mixture is clear and colorless and has a viscosity at 25° C. of 2,016 mPas.

The mixture, which is ready for use, contains 1.51% by weight of —HN—CO—NH— and 3.96% by weight of terminally bonded alkoxysilyl groups and, additionally, 50% by weight of tetraethoxysilane.

EXAMPLE 5

(a) Component A 0.2 part by weight of camphorquinone, 0.1 part by weight of 3,5-di-tert.-butyl-4-hydroxytoluene and 0.5 part by weight of N-diallyl-4-N,N-dimethylaminobenzenesulphonamide are dissolved in a mixture of 40 parts by weight of silicopolyether (Example 1) and 60 parts by weight of triethylene glycol dimethacrylate.

(b) Component B 4.1 parts by weight of 2-hydroxyethyl methacrylate are mixed with 3.5 parts by weight of normal hydrochloric acid.

If 10 parts by weight of component A are mixed with 1 part by weight of Component B, the mixture cures in 5 minutes to give an elastic body.

If this body is irradiated with a commercially available dental lamp (for example LCU, made by Bayer) or in a commercially available light oven (for example Dentacolor XS, made by Kulzer), the body cures to give a rigid material.

EXAMPLE 6

Base paste 41.7 parts by weight of a solution, consisting of 20 parts by weight of silicopolyether (of Example 2), 56 parts by weight of 2,2-bis-4-(3-methacryloxy-2-hydroxypropyl)-phenyl-propane, 23.2 parts by weight of triethylene glycol dimethacrylate, 0.2 part by weight of camphorquinone, 0.1 part by weight of 3,5-di-tert.-butyl-4-hydroxytoluene and 0.5 part by weight of N-diallyl-4-N,N-dimethylaminobenzenesulphonamide are processed with 58.3 parts by weight of a glass which had been surface-treated by conventional methods (for example glass GM 27884 k/6, made by Schott, having a C value of 2.1%) to give a paste.

If 10 parts of this base paste are mixed with 1 part by weight of component B of Example 5, the mixture cures in 10 minutes to give an elastic body.

If this body is irradiated for 60 seconds in a commercially available light oven (for example Dentacolor XS, made by Kulzer), a solid body of a flexural strength of 62 N/mm², a flexural modulus of 2,400 N/mm² and a water uptake of 3.6 mg/cm² is obtained.

EXAMPLE 7

41.7 parts by weight of a solution consisting of 20 parts by weight of silicopolyether (of Example 2), 55 parts by weight of 2,2-bis-[4-(3-methacryloxy-2-hydroxypropyl)-phenyl]-propane, 22.9 parts by weight of benzoyl peroxide and 0.1 part by weight of 3,5-di-tert.-butyl-4-hydroxytoluene, are processed with 58.3 parts by weight of a glass which had been surface-treated by conventional methods (for example glass GM 27884 k6, made by Schott, having a C value of 2.1%) to give a paste.

If 10 parts of this base paste are mixed with 1 part by weight of component B of Example 5, the mixture cures in 10 minutes to give an elastic body.

If this body is immersed for 20 minutes in boiling water, a solid body of a flexural strength of 69 N/mm² and a flexural modulus of 2700 N/mm² is obtained.

It will be appreciated that the instant specification and claims are set forth by way of illustration and not limitation, and that various modifications and changes may be made without departing from the spirit and scope of the present invention.

What is claimed is:

1. A two-component system which upon mixing forms a mixture curable in a series of steps to form a plastic material comprising a first component containing at least one monomer which can be subjected to free-radical curing at high temperature, low temperature or under the influence of light and at least one catalyst capable of causing condensation of a silicopolyether contained in a second component and a second component containing at least one silicopolyether capable of being condensed by the catalyst in the first component and at least one catalyst capable of causing the curing of the at least one monomer in the first component under the influence of high temperature, low temperature or light, wherein the silicopolyether comprises a polyaddition product containing ether, urethane and urea groups and having alkoxysilyl terminal groups of a mostly linear molecular structure, with exclusively aliphatically or cycloaliphatically bonded ether, urethane and urea segments, having a mean molecular weight Mn of 800–20,000, wherein said polyaddition product contains a) polyether groups in an amount of 25 to 90 parts by weight, per 100 parts by weight of polyaddition product, b) urethane groups

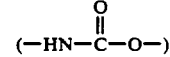

in an amount of 0.5 to 10 parts by weight, per 100 parts by weight of polyaddition product, c) urea groups

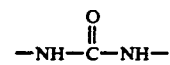

in an amount of 0.5 to 10 parts by weight, per 100 parts by weight of polyaddition product, and d) terminal alkoxysilyl groups

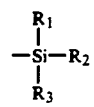

in an amount of 1 to 25 parts by weight, per 100 parts by weight of polyaddition product, the alkoxysilyl groups in the polyadduct being introduced by means of the following compounds which have the following formula:

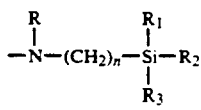

where
n represents the numbers 1 to 6,
R denotes hydrogen or —$(CH_2)_n$—$SiR_1R_2R_3$,
$R_1$ denotes $C_1$-$C_4$-alkoxy,
$R_2$ and $R_3$ have the same meaning as $R_1$ and additionally represent the methyl or the ethyl group,
the monomer which can be subjected to free radical curing comprises at least one methacrylate in monofunctional or polyfunctional form, and the catalyst for curing the monomer comprises at least one catalyst for hot, cold or solution polymerization.

2. A two component system according to claim 1, wherein after mixing the components the methacrylates are contained in the mixture with the silicopolyether in amounts of 10 to 90% by weight, based on the silicopolyether.

3. A two-component system according to claim 1, wherein the catalysts which are suitable for polymerization at high temperature, low temperature and under the influence of light are present in amounts of 0.01 to 10% by weight, based on the polymerizable material.

4. A plastic material obtained by curing in a series of steps and which is obtained by mixing and curing at least one silicopolyether, at least one monomer which can be subjected to free-radical curing, and at least one catalyst for polymerization at high temperature, low temperature and under the influence of light, and at least one catalyst for the condensation of the silicopolyether,
wherein the silicopolyether comprises a polyaddition product containing ether, urethane and urea groups and having alkoxysilyl terminal groups of a mostly linear molecular structure, with exclusively aliphatically or cycloaliphatically bonded ether, urethane and urea segments, having a mean molecular weight Mn of 800–20,000,
wherein said polyaddition product contains
a) polyether groups in an amount of 25 to 90 parts by weight, per 100 parts by weight of polyaddition product,
b) urethane groups

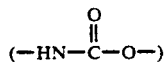

in an amount of 0.5 to 10 parts by weight, per 100 parts by weight of polyaddition product,
c) urea groups

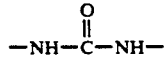

in an amount of 0.5 to 10 parts by weight, per 100 parts by weight of polyaddition product, and
d) terminal alkoxysilyl groups

in an amount of 1 to 25 parts by weight, per 100 parts by weight of polyaddition product, the alkoxysilyl groups in the polyadduct being introduced by means of the following compounds which have the following formula:

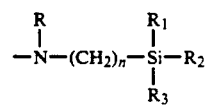

where
n represents the numbers 1 to 6,
R denotes hydrogen or —$(CH_2)_n$—$SiR_1R_2R_3$,
$R_1$ denotes $C_1$-$C_4$-alkoxy,
$R_2$ and $R_3$ have the same meaning as $R_1$ and additionally represent the methyl or the ethyl group,
the monomer which can be subjected to free radical curing comprises at least one methacrylate in monofunctional or polyfunctional form, and the catalyst for curing the monomer comprises at least one catalyst for hot, cold or solution polymerization.

5. A plastic material according to claim 4, wherein the methacrylates are contained in the mixture with the silicopolyether in amounts of 10 to 90% by weight, based on the silicopolyether.

6. A plastic material according to claim 4 wherein the catalysts which are suitable for polymerization of high temperature, low temperature and under the influence of light are present in amounts of 0.01 to 10% by weight, based on the polymerizable material.

* * * * *